United States Patent
Cobain

(10) Patent No.: US 8,529,456 B2
(45) Date of Patent: *Sep. 10, 2013

(54) HEART AGE ASSESSMENT

(71) Applicant: Conopco, Inc., Englewood Cliffs, NJ (US)

(72) Inventor: Mark Robert Cobain, Sharnbrook (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/671,709

(22) Filed: Nov. 8, 2012

(65) Prior Publication Data

US 2013/0073215 A1 Mar. 21, 2013

Related U.S. Application Data

(63) Continuation of application No. 12/151,048, filed on May 2, 2008, now Pat. No. 8,409,104.

(51) Int. Cl.
*A61B 5/02* (2006.01)

(52) U.S. Cl.
USPC .......................................... 600/481; 600/508

(58) Field of Classification Search
USPC ........................... 600/301, 483; 128/923–924
See application file for complete search history.

(56) References Cited

U.S. PATENT DOCUMENTS

| | | | |
|---|---|---|---|
| 6,024,281 A | 2/2000 | Shepley | |
| 6,602,469 B1 | 8/2003 | Maus et al. | 422/68.1 |
| 2004/0087864 A1 | 5/2004 | Grouse | 600/508 |
| 2005/0106449 A1 | 5/2005 | Fan et al. | |
| 2005/0261558 A1 | 11/2005 | Eaton et al. | 600/300 |
| 2009/0327204 A1 | 12/2009 | Gilhuly | 706/54 |

FOREIGN PATENT DOCUMENTS

JP 2003216735 A 7/2003

OTHER PUBLICATIONS

Hingorani, A simple computer program for guiding management of cardiovascular risk factors and prescribing, British Medical Journal, Jan. 9, 1999, 318, pp. 101-105.
Anderson et al., An Updated Coronary Risk Profile; A Statement for Health Professionals, Journal of the American Heart Association, 1991, pp. 356-362.
Wilson et al., Prediction of Coronary Heart Disease Using Risk Factor Categories, Journal of the American Heart Assosiation, May 12, 1998, 1837-1847.
International Search Report International Application No. PCT/EP2009/054754 mailed Jan. 22, 2010.
International Preliminary Report on Patentability International Application No. PCT/EP2009/054754 mailed Aug. 31, 2010.
Parikh et al., A Risk Score for Predicting Near-Term Incidence of Hypertension: The Framingham Heart Study, 2008, Annals of Internal Medicine, 148, p. 102-110,W-16.

*Primary Examiner* — Navin Natnithithadha
*Assistant Examiner* — Michael R Bloch
(74) *Attorney, Agent, or Firm* — Michael P. Aronson

(57) ABSTRACT

An automated method of determining a measure of a subject's heart age comprising the steps of: prompting a user for a plurality of inputs, each relating to an attribute of the subject, each attribute defining one or more of a demographic status of the subject, a lifestyle status of the subject, a physical condition of the subject and a medical history of the subject; receiving, from the user, a plurality of said inputs; determining from said received inputs, a set of parameters for which input data has been received as input from the user; selecting a heart age calculation algorithm from a predetermined set of heart age calculation algorithms according to said set of parameters; and calculating a heart age for the subject according to the selected algorithm; and providing as output said calculated heart age.

19 Claims, 3 Drawing Sheets

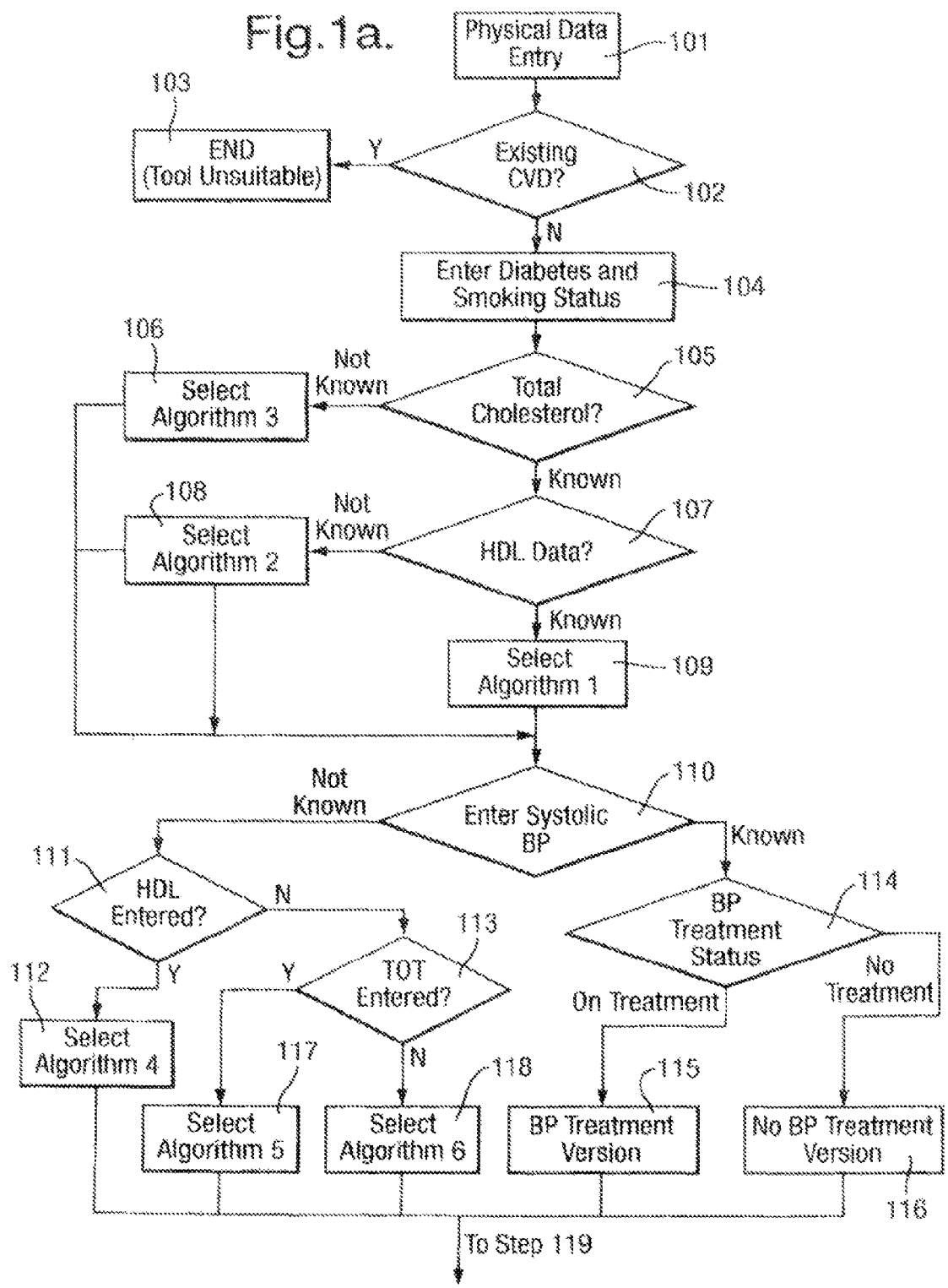

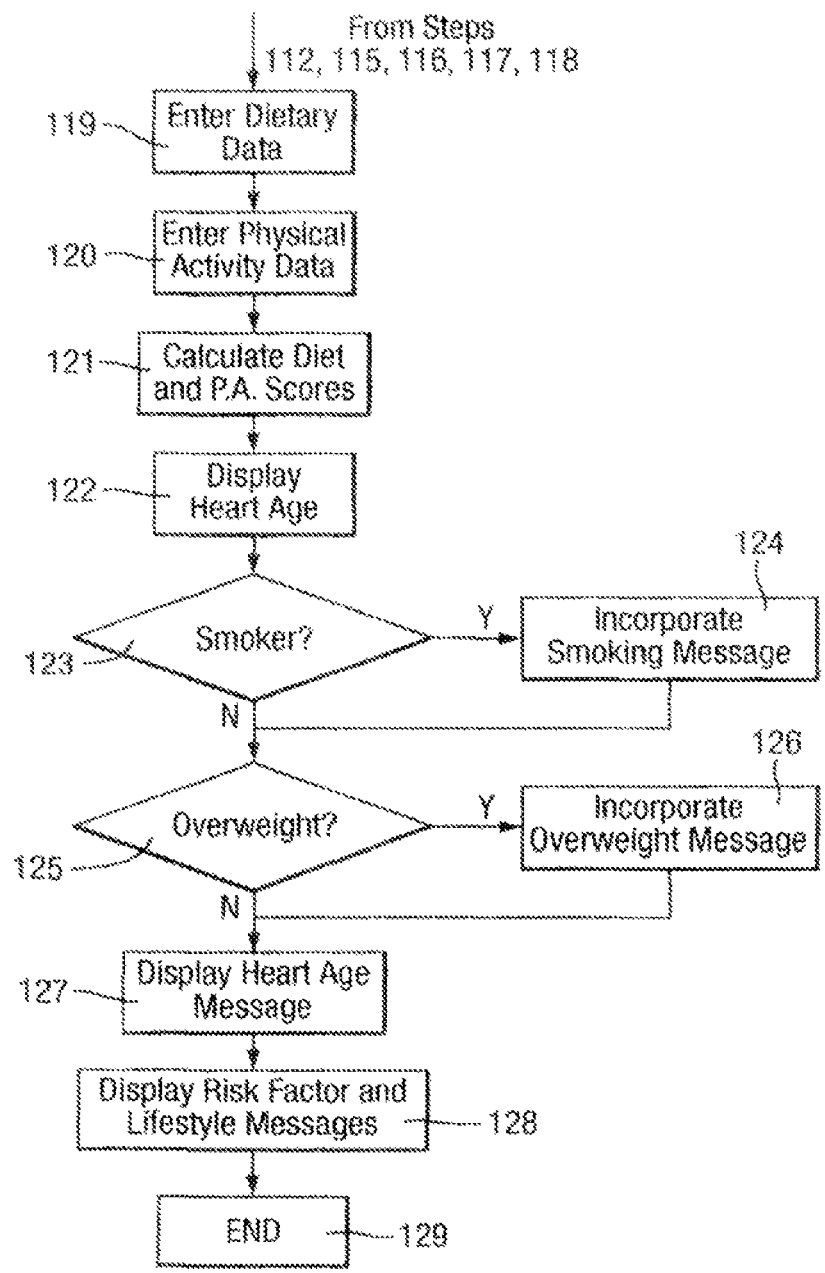

HEART AGE ASSESSMENT

Figure 2:
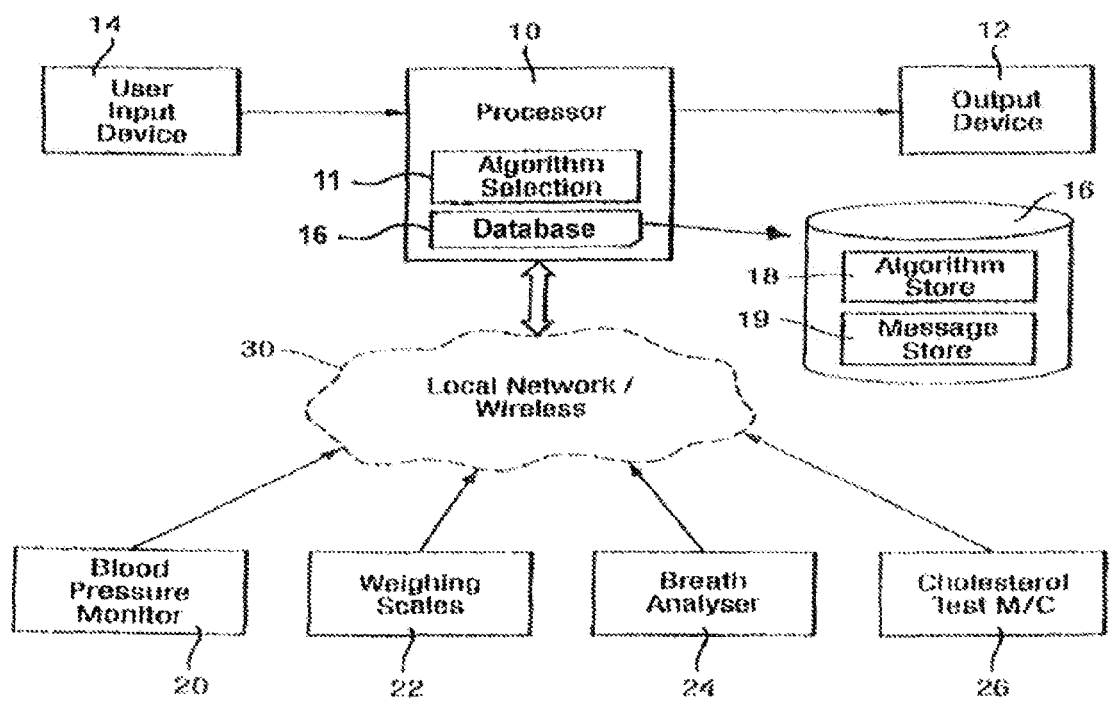

This is a Continuation Application of co-pending U.S. patent application Ser. No. 12/151,048, filed May 2, 2008 which is incorporated herein in its entirety, by reference.

FIELD OF THE INVENTION

The invention relates to assessment of heart age and to systems, devices and processes for promoting behaviours in a population through the use of such heart age assessments.

BACKGROUND

The listing or discussion of an apparently prior-published document in this specification should not necessarily be taken as an acknowledgement that the document is part of the state of the art or is common general knowledge.

Statistical models predicting the occurrence of CVD (cardiovascular disease), covering a range of conditions including fatal and non-fatal myocardial infarction, angina, transient ischemia, intermittent claudication and stroke, have been in existence for over thirty years, with the most prominent of these published by investigators from the Framingham Heart Study (Anderson et al., 1991, Wilson et al., 1998). These are used widely by clinicians in order to calculate an individual patient's risk of CVD and stratify patients for risk factor reduction, such as prescribing medication or recommending dietary changes and exercise regimens. The widespread use of such statistical models has been facilitated by their actual as well as perceived validity, as assessed by the capacity of risk scores derived from the models to predict CVD in multiple populations beyond the original study. This has led to risk scores being recommended in a number of international guidelines for cholesterol treatment in particular. The use of these models has also been facilitated by their simplicity, generally requiring input by clinicians of the results of simple tests of blood pressure, cholesterol, diabetic status and self reported smoking behaviour, together with development of simple "tools" designed to simplify the calculation process (using charts, software deployed on CD-ROM, internet or handheld digital devices). In particular, US 2005/0261558 discloses a tool implemented in logic on a computing device such as a PDA (Personal Digital Assistant) that permits a user to input patient-specific data relevant to evaluating risk for CVD and calculating an equivalent age of the patient, based on the Framingham data set and the input data.

Such developments have been of value to doctors and their patients. Further evaluation of methods for communicating risk to clinicians has led to the development of different risk framing methods. For example, an age-matched CVD risk has been demonstrated to increase the likelihood that individuals will perceive a high risk score (as computed by Framingham risk scores) to be high (Fair et al., 2008). Further elaboration on this concept to create a "cardiovascular disease risk adjusted age" (Goldman et al, 2006), or "Heart Age" (Goldman et al, 2006) has also shown to be well understood by patient populations. This is of critical importance since models of health behaviour highlight the importance that an individual needs to have a heightened sense of perceived susceptibility to disease before taking action.

Whilst clinicians have been the foot soldiers in the treatment of disease and prevention in high risk individuals, the global burden of cardiovascular disease is sustained by poor health in entire populations, necessitating a method for raising awareness of CVD risk outside clinical settings, i.e. in the wider population. In order to maximise the potential to reduce risk at a population level, it is important to penetrate the vast majority of the population to try and reduce CVD risk factors. Whilst clinicians are advised to prescribe cholesterol-lowering medication to those at 20% risk of CHD or greater (Adult Treatment Panel III, 2001), Ajani et al (2006) have estimated that just 13.7% of the US population fall into the >20% risk category, using NHANES (National Health and Nutrition Examination Survey) data. Furthermore, those with <10% risk who are deemed "low risk" by clinical standards comprise greater than 75% of the population. If the US population currently stands at more than 300 million, it follows that approximately 40 million people have the potential to have their CVD risk reduced by their clinician. Assuming that patients achieve a reduction in CVD risk of 5% using medication for lowering blood pressure and cholesterol, then the number of estimated primary CVD events in the subsequent ten years in this group will fall from 8 million to 6 million.

On the other hand, it also follows that approximately 225 million people are at <10% risk in the US population yet are much less likely to be targeted by clinicians for risk reduction purposes. Nevertheless up to 22.5 million people are estimated to have a primary CVD event in the subsequent ten years from this group, far in excess of those estimated as likely to have events in the high risk population. Furthermore, to achieve a similar magnitude of risk reduction in this population (i.e. 2 million events) the risk need only be reduced by <1%. The greater potential of this approach is adequately demonstrated by the fact that a risk reduction of 2% could lead to over 4.5 million CVD events being prevented.

An individual user's heart age can be defined as being the chronological age of a population that is at a low or normal risk of cardiovascular disease for their age, and whose risk of CVD is closest or equal to that of the individual user. The heart age is consequently the age at which an individual's measured cardiovascular risk would be defined as "normal" according to international guidelines.

A major challenge exists in estimating heart age outside of clinical settings, given the measurements that are generally required to calculate a valid estimate. For example, serum total cholesterol and HDL (high-density lipoprotein) cholesterol require a blood sample to be taken, which reduces the convenience to users and increases costs. Therefore new methods are required for optimising the process of estimating heart age according to the measures that may be available. These estimates should not, however, be generated at the expense of other more accurate CVD risk estimates, nor should such estimates fail to identify those who may require further blood tests for determining a possible high risk status (e.g. diabetes or hypercholesterolemia). Often such decisions are a question of cost and so the capability to alter the thresholds for these finding such "cases" should be adaptable based on the resource needs of a particular country.

Ajani et al estimated from the NHANES survey that 60.8% of those with 10% risk and 74.1% of those with 10-20% risk are overweight in the US population. Critically, overweight status is associated with 1) increased prevalence of CVD risk factors (blood pressure, diabetes, high total cholesterol, low HDL cholesterol) included in the Framingham Risk Score and 2) increased risk of incident CVD risk factors included in the Framingham risk score or changes in CVD risk factors over time. Therefore targeting a "heart health" message to populations at <20% risk leading to a change in health behaviours consistent with a risk factor reduction would have substantial public health benefits.

Finally, whilst cholesterol is inconvenient to measure on a large scale messages about cholesterol lowering should still be promoted to individuals within a population. Therefore, it is important that any method should have the capability to estimate a range of cholesterol values to which an individual can be assigned to if that individual chooses not to or is unable to take a blood test.

It is an object of the invention to address one or more of the above mentioned problems.

SUMMARY OF THE INVENTION

In accordance with one aspect of the invention there is provided an automated method of determining a measure of a subject's heart age comprising the steps of:
receiving a plurality of inputs, each relating to an attribute of the subject, each attribute defining one or more of a demographic status of the subject, a lifestyle status of the subject, a physical condition of the subject and a medical history of the subject; determining from said received inputs, a set of parameters for which input data has been received as input;
selecting a heart age calculation algorithm from a predetermined set of heart age calculation algorithms according to said set of parameters;
calculating a heart age for the subject according to the selected algorithm; and
providing as output said calculated heart age.

In accordance with another aspect of the invention there is provided an apparatus for determining a measure of a subject's heart age, the apparatus comprising:
means for receiving a plurality of inputs, each relating to an attribute of the subject, each attribute defining one or more of a demographic status of the subject, a lifestyle status of the subject, a physical condition of the subject and a medical history of the subject;
means for determining from said received inputs, a set of parameters for which input data has been received;
means for selecting a heart age calculation algorithm from a predetermined set of heart age calculation algorithms according to said set of parameters;
means for calculating a heart age for the subject according to the selected algorithm; and
means for providing as output said calculated heart age.

In accordance with another aspect of the invention there is provided an automated method of estimating blood lipid levels of a subject comprising the steps of:
a) receiving a plurality of data values, each relating to an attribute of the subject, each attribute defining one or more of a demographic status of the subject, a lifestyle status of the subject, a physical condition of the subject and a medical history of the subject, the data values not including any quantitative measure of a cholesterol level of the subject;
b) calculating a first CVD risk for the subject based on said data values using a first algorithm;
c) determining one or a range of possible total cholesterol levels and HDL cholesterol levels for the subject consistent with the calculated first CVD risk by comparison of the first CVD risk with statistical average CVD risk as a function of measured total and HDL cholesterol levels in a population;
d) determining a statistical average total cholesterol level in a population for the subject's age and/or gender; and
e) calculating an estimated HDL cholesterol level for the subject as a function of the first CVD risk and the determined statistical average total cholesterol level in the population.

In accordance with another aspect of the invention there is provided an apparatus for estimating blood lipid levels of a subject, the apparatus comprising:
a) means for receiving a plurality of data values, each relating to an attribute of the subject, each attribute defining one or more of a demographic status of the subject, a lifestyle status of the subject, a physical condition of the subject and a medical history of the subject, the data values not including any quantitative measure of a cholesterol level of the subject;
b) means for calculating a first CVD risk for the subject based on said data values using a first algorithm;
c) means for determining one or a range of possible total cholesterol levels and HDL cholesterol levels for the subject consistent with the calculated first CVD risk by comparison of the first CVD risk with statistical average CVD risk as a function of measured total and HDL cholesterol levels in a population;
d) means for determining a statistical average total cholesterol level in a population for the subject's age and/or gender;
e) means for calculating an estimated HDL cholesterol level for the subject as a function of the first CVD risk and the determined statistical average total cholesterol level in the population.

In accordance with another aspect of the invention there is provided an apparatus for assisting a user in making beneficial food choices while shopping comprising:
means for receiving a user's heart age;
means for determining a recommended maximum proportion of saturated fat in the user's diet based on said user's heart age;
output means for providing as output, indications of recommended food products falling within the recommended maximum proportion of saturated fat in the user's diet for the user's heart age.

Embodiments of the invention will now be described, by way of example and with reference to the accompanying drawings in which:

FIGS. 1a and 1b illustrate a flow chart of an exemplary process for determining a heart age of a user; and FIG. 2 shows a schematic diagram of an apparatus suitable for determining a heart age of a user.

DETAILED DESCRIPTION

Given the ability of the "heart age" message to increase perception of CVD risk in those who are exposed to it, a capability to provide this score to as many people in the population at a given time is of great public health importance. In order to do so, valid systems, processes and tools for predicting heart age are required that can be used in the population outside the confines of a clinician's office. In order to maintain focus on risk factors that have proven to be predictive of CVD, health behaviours that are promoted should be clearly related to a reduction in those risk factors. Exemplary behaviours include particular dietary changes that are predicted to reduce blood pressure or serum cholesterol (or both).

In order to optimise the heart age of individuals within a population, success of a particular behaviour change should be ultimately defined by a reduction in CVD risk factors, which themselves lead to a lowering of heart age. However, given the time taken for lifestyle changes to reduce CVD risk factors (typically in the range of weeks to months), a number of heart age leading indicators can be developed to assess progress towards a lower heart age. This serves the purpose of ascertaining the impact of the heart age on behaviour change and provides a reinforcement mechanism to reward individuals making such changes. These are partly analogous to secondary outcomes in clinical trials, with the heart age score being the primary outcome of interest.

Such tools preferably comply with the following criteria:
1) Validity: A tool should calculate a heart age score that has proven ability to predict CVD in the population, as evidenced by peer reviewed publication.
2) Population capacity: A tool should have the scope to be used by the majority within the population in a manner that is acceptable from a cost and convenience perspective (to both clinical practitioners and users within the population).
3) "Heart Age Behaviour Change": A tool should have the ability to promote health behaviour change that will lead to reductions in CVD risk factors and thereby heart age. Given that such reductions in CVD risk factors may take time, a projected impact on heart age over a given time period should be computed without impact on criteria 1 or 2. Any tool should also have the capability to evaluate heart age for a given individual after having made the changes A method for calculating an individual's "real age" has been proposed previously and exists on consumer web sites e.g. "RealAge.com". These are lifestyle questionnaires that meet criterion 2 (in that they can be used by individuals in the population without recourse to clinical measures). It is debatable that they meet the criterion 3 (leads to some form of change in lifestyle that reduces cardiovascular risk factors) as no evidence has been put forward for this. Such questionnaires do not meet the requirements of criterion 1, since none of the tools for calculating a "real age" have been constructed within a real data-set, but rather from a mixed set of literature. Furthermore, for a tool to give a meaningful prediction of health outcomes, the tool should be validated in a data-set separate from that on which it has been generated. Without a valid connection to CVD risk, the health impact on populations is impossible to define.

An alternative approach is to use clinical CVD tools to create risk and calculate age appropriate risk values. The main barrier to extended use of such an approach is the inconvenience and cost to the user. To take one example, the cost of a blood test for serum lipoproteins (Total, HDL, LDL) is approximately $50 per patient, whilst diabetes diagnosis through oral glucose tolerance tests can cost significantly more if the long duration of the test is considered. Furthermore, the inconvenience to patients associated with taking the test may reduce the likelihood of an individual coming forward for health screening and certainly limits the validity of the risk score outside this setting. This is particularly important in countries or regions where lower levels of resource are available for health screening.

Therefore a method of the present invention proposes to meet all 3 criteria for the development of a population-based heart age measurement, solving the problems associated with lifestyle questionnaires by including validated risk functions as the basis for the heart age calculation, thereby identifying individuals at real risk in the population. The method also solves the problems of clinical-based heart age scores by incorporating non invasive measures into risk scores and imputing estimated values for risk factors that may require inconvenient and costly blood tests. The method therefore is able to maximise the benefits of CVD risk calculation for the lowest possible cost.

Benefits of the invention include the ability to provide a valid measurement that is predictive of age-matched cardiovascular risk, that promotes awareness and understanding of CVD risk, and that can therefore lead to a change in health behaviour outcomes. Such health behaviour outcomes may include:

a) A change in diet consistent with cholesterol lowering guidelines
b) A change in diet consistent with blood pressure lowering guidelines
c) Smoking cessation
d) An increase in physical activity
e) Greater adherence to risk factor reduction regime (e.g. medication, dietary plan etc)
f) Weight loss efforts
g) Willingness to undergo health screening (blood tests, physical measurements)

Each of the above outcomes can be associated with a decrease in CVD risk, and a consequent reduction in heart age.

The calculation of heart age involves obtaining an individual's risk factors, which each relate to an attribute of that individual or subject. The most important risk factors, with the expected responses for being input into a system for calculating heart age, are as follows:
gender (m/f)
age (years)
total cholesterol (e.g. in mg/dl or other appropriate unit)
HDL cholesterol (same units as for total cholesterol)
systolic blood pressure (mmHg)
prevalent diabetes (yes/no)
smoker within the past year (yes/no)
antihypertensive treatment within the past year (yes/no)

Each of these risk factors or attributes of the subject individual effectively comprises a parameter defining one or more of a demographic status of the subject (e.g. age and gender), a lifestyle status of the subject (e.g. smoking), a physical condition of the subject (e.g. cholesterol level, blood pressure level, etc) and a medical history of the subject (e.g. incidence of diabetes or hypertension, etc). Other attributes may be considered.

The above risk factors can be used to obtain an estimate of the probability of CVD incidence within the next 10 years, for example through use of the Framingham dataset. CVD in this case is defined as being the composite endpoint of coronary heart disease (including angina pectoris), stroke (including transient ischemic attacks), intermittent claudication, congestive heart failure or death due to any of these causes.

The following algorithms 1 to 5 can be used to determine an estimate of the probability of incident CVD and heart age, depending on which of the above risk factors are available from an individual. A choice of algorithm can be automatically made depending on answers received from the user. For each algorithm, it is assumed that basic non-invasive data on the user is available as required, such as age, weight, gender, height and waist measurement. Each algorithm is tailored according to the presence or absence of the remaining risk factors given above.

Algorithm 1

This algorithm may be used when total cholesterol, HDL cholesterol and systolic blood pressure are all known. The 10-year probability of CVD can be calculated as follows:

For men on antihypertensive treatment:

$$CVDRisk = 1 - 0.88936^x \quad x = e^{3.06117\ ln(Age) + 1.12370\ ln(TOT) - 0.93263\ ln(HDL) + 0.57367(DIAB) + 0.65451(SMK) + 1.99881\ ln(SBP) - 23.9802}$$ [equation 1]

For men not on antihypertensive treatment:

$$CVDRisk = 1 - 0.88936^x \quad x = e^{3.06117\ ln(Age) + 1.12370\ ln(TOT) - 0.93263\ ln(HDL) + 0.57367(DIAB) + 0.65451(SMK) + 1.99303\ ln(SBP) - 23.9802}$$ [equation 2]

For women on antihypertensive treatment:

$$CVDRisk = 1 - 0.95012^x, x = e^{2.32888\, ln(Age) + 1.20904\, ln(TOT) - 0.70833\, ln(HDL) + 0.69154(DIAB) + 0.52873(SBP) + 2.82263\, ln(SBP) - 26.1931}$$ [equation 3]

For women not on antihypertensive treatment:

$$CVDRisk = 1 - 0.95012^x, x = e^{2.32888\, ln(Age) + 1.20904\, ln(TOT) - 0.70833\, ln(HDL) + 0.69154(DIAB) + 0.52873(SMK) + 2.76157\, ln(SHP) - 26.1931}$$ [equation 4]

where TOT is total cholesterol, HDL is the HDL cholesterol, DIAB is 1 if prevalent diabetes and 0 otherwise, SMK is 1 if smoking is indicated in the past year and 0 otherwise, and SBP is systolic blood pressure.

Once an individual's 10-year CVD probability is calculated using any one of the equations 1 to 4 above, the algorithm then finds the age corresponding to someone of the same gender who has the same CVD probability but who has a low to normal risk factor profile. Such a profile may for example comprise the following factors:

total cholesterol=180 mg/dl
HDL=45 mg/dl
SBP=125 mmHg (130 mmHg if the subject is aged 60 or over)
No diabetes (DIAB=0)
No smoking in past year (SMK=0)
No hypertensive treatment The resulting age from the following calculations is the individual's estimated heart age. The numbers in parentheses within the denominator terms represent set values for the risk factors outlined above. These may be modified according to shifting definitions of what represents a "low to normal" risk factor profile. Such numbers may change over time and may vary by national requirement (often as a function of available resources to treat "high" risk factor profiles)

For men:

$$HeartAge = \frac{1}{e^{3.06117}} ln\left(\frac{log_{0.88936}(1 - CVDRisk)}{e^{1.12370\, ln(180) - 0.93263\, ln(45) + 1.93303\, ln(125) - 23.9802}}\right)$$ [equation 5]

For women:

$$HeartAge = \frac{1}{e^{2.32888}} ln\left(\frac{log_{0.95012}(1 - CVDRisk)}{e^{1.20904\, ln(180) - 0.70833\, ln(45) + 2.76157\, ln(125) - 26.1931}}\right)$$ [equation 6]

Algorithm 2

This algorithm may be used when the total cholesterol, systolic blood pressure and body mass index (BMI) are known, but where HDL cholesterol is not known. The 10-year probability of CVD can be calculated as follows:

For men on antihypertensive treatment:

$$CVDRisk = 1 - 0.88675^x, x = e^{3.03720\, ln(Age) + 1.01760\, ln(TOT) + 0.74442\, ln(BMI) + 0.57908(DIAB) + 0.69055(SMK) + 1.83625\, ln(SBP) - 28.4748}$$ [equation 7]

For men not on antihypertensive treatment:

$$CVDRisk = 1 - 0.88675^x, x = e^{3.03720\, ln(Age) + 1.01760\, ln(TOT) + 0.74442\, ln(BMI) + 0.57908(DIAB) + 0.69055(SMK) + 1.76320\, ln(SBP) - 28.4748}$$ [equation 8]

For women on antihypertensive treatment:

$$CVDRisk = 1 - 0.94995^x, x = e^{2.32017\, ln(Age) + 1.18269\, ln(TOT) + 0.53748\, ln(BMI) + 0.75827(DIAB) + 0.60285(SMK) + 2.75689\, ln(SBP) - 30.2760}$$ [equation 9]

For women not on antihypertensive treatment:

$$CVDRisk = 1 - 0.94995^x, x = e^{2.32017\, ln(Age) + 1.18269\, ln(TOT) + 0.53748\, ln(BMI) + 0.75827(DIAB) + 0.60285(SMK) + 2.69017\, ln(SBP) - 30.2760}$$ [equation 10]

Once an individual's 10-year CVD probability is calculated using any one of the equations 7 to 10 above, the algorithm then finds the individual's heart age as for algorithm 1, but using a low-normal value BMI value of 22, in place of an HDL value. As is the case in algorithm 1, changes in risk factor values may be modified according to shifting definitions of what represents a "low to normal" risk factor profile. Such numbers may change over time and may vary by national requirement The resulting age from the following calculations is the individual's estimated heart age.

For men:

$$HeartAge = \frac{1}{e^{3.03720}} ln\left(\frac{log_{0.88675}(1 - CVDRisk)}{e^{1.01760\, ln(180) + 0.74442\, ln(22) = 1.76320\, ln(125) - 28.4748}}\right)$$ [equation 11]

For women:

$$HeartAge = \frac{1}{e^{2.32017}} ln\left(\frac{log_{0.94995}(1 - CVDRisk)}{e^{1.18269\, ln(180) + 0.53748\, ln(22) + 2.69017\, ln(125) - 30.2760}}\right)$$ [equation 12]

Algorithm 3

This algorithm may be used when the total cholesterol and HDL cholesterol are unknown, but the BMI and systolic blood pressure are known. The 10-year probability of CVD can be calculated as follows:

For men on antihypertensive treatment:

$$CVDRisk = 1 - 0.88431^x, x = e^{3.11296\, ln(Age) + 0.79277\, ln(BMI) + 0.53160(DIAB) + 0.70953(SMK) + 1.92672\, ln(SBP) - 23.9388}$$ [equation 13]

For men not on antihypertensive treatment:

$$CVDRisk = 1 - 0.88431^x, x = e^{3.11296\, ln(Age) + 0.79277\, ln(BMI) + 0.53160(DIAB) + 0.70953(SMK) + 1.85508\, ln(SBP) - 23.9388}$$ [equation 14]

For women on antihypertensive treatment:

$$CVDRisk = 1 - 0.94833^x, x = e^{2.72107\, ln(Age) + 0.51125\, ln(BMI) + 0.77763(DIAB) + 0.61868(SMK) + 2.88267\, ln(SBP) - 26.0145}$$ [equation 15]

For women not on antihypertensive treatment:

$$CVDRisk = 1 - 0.94833^x, x = e^{2.72107\, ln(Age) + 0.51125\, ln(BMI) + 0.77763(DIAB) + 0.61868(SMK) + 2.81291\, ln(SBP) - 26.0145}$$ [equation 16]

where TOT is total cholesterol, HDL is the HDL cholesterol, DIAB is 1 if prevalent diabetes and 0 otherwise, SMK is 1 if smoking is indicated in the past year and 0 otherwise, and SBP is systolic blood pressure.

Once an individual's 10-year CVD probability is calculated using any one of the equations 13 to 16 above, the algorithm then finds the age corresponding to someone of the same gender who has the same CVD probability but who has a low to normal risk factor profile. Such a profile may for example comprise the following factors:

BMI=22
SBP=125 mmHg (130 mmHg if the subject is aged 60 or over)
No diabetes (DIAB=0)
No smoking in past year (SMK=0)
No hypertensive treatment As is the case in algorithm 1 changes in risk factor values may be modified according to shifting definitions of what represents a "low to normal" risk factor profile. Such numbers may change over time and may vary by national requirement.

The resulting age from the following calculations is the individual's estimated heart age.

For men:

$$HeartAge = \frac{1}{e^{3.11296}} \ln\left(\frac{\log_{0.88431}(1-CVDRisk)}{e^{0.79277 ln(22)+1.85508 ln(125)-23.9388}}\right) \quad [\text{equation 17}]$$

For women:

$$HeartAge = \frac{1}{e^{3.11296}} \ln\left(\frac{\log_{0.88431}(1-CVDRisk)}{e^{0.79277 ln(22)+1.85508 ln(125)-23.9388}}\right) \quad [\text{equation 18}]$$

Algorithm 4

This algorithm may be used when the total cholesterol and HDL cholesterol are known, but systolic blood pressure is not known. The 10-year probability of CVD can be calculated as follows:

For men:

$$CVDRisk=1-0.88970^x x=e^{3.22476\ ln(Age)+1.11551}$$
$$ln(TOT)-0.93052\ ln(HDL)+0.58180(HTN)+0.64151(DIAB)+$$
$$0.63505(SMK)-15.3561 \quad [\text{equation 19}]$$

For women:

$$CVDRisk=1-0.94875^x x=e^{2.74587\ ln(Age)+1.32797}$$
$$ln(TOT)-0.75601\ ln(HDL)+0.71993(HTN)+0.70137(DIAB)+$$
$$0.52307(SMK)-15.1058 \quad [\text{equation 20}]$$

where HTN is 1 if the individual has been diagnosed as hypertensive or is on antihypertensive treatment and 0 otherwise.

Once an individual's 10-year CVD probability is calculated using equation 19 or 20 above, the algorithm then finds the age corresponding to someone of the same gender who has the same CVD probability but who has a low to normal risk factor profile. Such a profile may for example comprise the following factors:

Total cholesterol=180 mg/di
HDL=45 mg/di
No diabetes (DIAB=0)
No smoking in past year (SMK=0)
No hypertension (HTN=0)

As is the case in algorithm 1 changes in risk factor values may be modified according to shifting definitions of what represents a "low to normal" risk factor profile. Such numbers may change over time and may vary by national requirement.

The resulting age from the following calculations is the individual's estimated heart age.

For men:

$$HeartAge = \frac{1}{e^{3.22476}} \ln\left(\frac{\log_{0.88970}(1-CVDRisk)}{e^{1.11551 ln(180)-0.93042 ln(45)-15.3561}}\right) \quad [\text{equation 21}]$$

For women:

$$HeartAge = \frac{1}{e^{2.74587}} \ln\left(\frac{\log_{0.94375}(1-CVDRisk)}{e^{1.32797 ln(180)-0.75601 ln(45)-15.1058}}\right) \quad [\text{equation 22}]$$

Algorithm 5

This algorithm is to be used when the total cholesterol and BMI are known, but when systolic blood pressure and HDL are not known. The 10-year probability of CVD can be calculated as follows:

For men:

$$CVDRisk=1-0.88675^x x=e^{3.17473\ ln(Age)+1.01090}$$
$$ln(TOT)+0.81298\ ln(BMI)+0.55059(HTN)+0.64062(DIAB)+$$
$$0.66596(SMK)-20.4549 \quad [\text{equation 23}]$$

For women:

$$CVDRisk=1-0.94869^x x=e^{2.72740\ ln(Age)+1.29051}$$
$$ln(TOT)+0.73896\ ln(BMI)+0.69964(HTN)+0.76749(DIAB)+$$
$$0.60289(SMK)-20.2670 \quad [\text{equation 24}]$$

where, as for algorithm 4, HTN is 1 if the individual has been diagnosed as hypertensive or is on antihypertensive treatment and 0 otherwise.

Once an individual's 10-year CVD probability is calculated using equation 23 or 24 above, the algorithm then finds the age corresponding to someone of the same gender who has the same CVD probability but who has a low to normal risk factor profile. Such a profile may for example comprise the following factors:

Total cholesterol=180 mg/di
BMI=22
No diabetes (DIAB=0)
No smoking in past year (SMK=0)
No hypertension (HTN=0)

As is the case in algorithm 1 changes in risk factor values may be modified according to shifting definitions of what represents a "low to normal" risk factor profile. Such numbers may change over time and may vary by national requirement.

The resulting age from the following calculations is the individual's estimated heart age.

For men:

$$HeartAge = \frac{1}{e^{3.17473}} \ln\left(\frac{\log_{0.88675}(1-CVDRisk)}{e^{1.01090 ln(180)-0.71298 ln(22)-20.4549}}\right) \quad [\text{equation 25}]$$

For women:

$$HeartAge = \frac{1}{e^{2.72740}} \ln\left(\frac{\log_{0.94869}(1-CVDRisk)}{e^{1.2905 ln(180)-0.73896 ln(22)-20.2670}}\right) \quad [\text{equation 26}]$$

Algorithm 6

This algorithm is to be used when the total cholesterol, HDL and systolic blood pressure are unknown, but BMI is known. The 10-year probability of CVD can be calculated as follows:

For men:

$$CVDRisk=1-0.88434^x x=e^{3.25024\ ln(Age)+0.74711}$$
$$ln(BMI)+0.57695(HTN)+0.59741(DIAB)+0.68506(SMK)-$$
$$15.4710 \quad [\text{equation 27}]$$

For women:

$$CVDRisk=1-0.94679^x x=e^{3.18736\ ln(Age)+0.72923}$$
$$ln(BMI)+0.73404(HTN)+0.78285(DIAB)+0.61608(SMK)-$$
$$15.1252 \quad [\text{equation 28}]$$

where, as for algorithm 4, HTN is 1 if the individual has been diagnosed as hypertensive or is on antihypertensive treatment and 0 otherwise. Once an individual's 10-year CVD probability is calculated using equation 27 or 28 above, the algorithm then finds the age corresponding to someone of the same gender who has the same CVD probability but who has a low to normal risk factor profile. Such a profile may for example comprise the following factors:

BMI=22
No diabetes (DIAB=0)
No smoking in past year (SMK=0)
No hypertension(HTN=0)

As is the case in algorithm 1 changes in risk factor values may be modified according to shifting definitions of what represents a "low to normal" risk factor profile. Such numbers may change over time and may vary by national requirement.

The resulting age from the following calculations is the individual's estimated heart age.

For men:

$$HeartAge = \frac{1}{e^{3.25024}} \ln\left(\frac{\log_{0.88434}(1 - CVDRisk)}{e^{0.74711 ln(22) - 15.4710}}\right) \quad \text{[equation 29]}$$

For women:

$$HeartAge = \frac{1}{e^{3.18736}} \ln\left(\frac{\log_{0.94679}(1 - CVDRisk)}{e^{0.72923 ln(22) - 15.1252}}\right) \quad \text{[equation 30]}$$

As will be seen from the different calculations above, different weightings are placed on the different variables used, depending on the available information. Algorithm 1 may be considered a higher standard by which the other algorithms are ultimately compared, since algorithm 1 takes into account the most factors that can be modified by an individual to lower their risk. Algorithms 2 to 6 take into account progressively fewer (and different) variables, and within them have new weightings as a result of the omission of some variables and replacement with others, such as the replacement of HDL with BMI in algorithms 2, 3, 5 and 6.

The table below summarises the various inputs required for each algorithm, indicated by an 'x' in the relevant column for each algorithm A1 to A6.

| Algorithm | Age | Gender | Total | HDL | DIAB | SMK | SBP | HTN | BMI |
|---|---|---|---|---|---|---|---|---|---|
| A1 | x | x | x | x | x | x | x | x | |
| A2 | x | x | x | | x | x | x | x | x |
| A3 | x | x | | | x | x | x | x | x |
| A4 | x | x | x | x | x | x | | x | |
| A5 | x | x | x | | x | x | | x | x |
| A6 | x | x | | | x | x | | x | x |

The algorithms generally fall into two classes, a first class of which contain cholesterol level as an input parameter and a second class of which do not contain cholesterol as an input parameter. As discussed above, although the use of cholesterol levels as input parameters can provide a more accurate assessment of heart age, it is useful to provide an alternative algorithm not requiring cholesterol level as an input parameter, particularly for frequent monitoring and feedback to the user in view of the high cost and inconvenience of the blood tests required.

The algorithms above exemplify preferred versions that have been found to offer particularly good correlation with existing clinically derived data. However, it will be understood that minor changes in the exact values may be made to fine tune accuracy to other and/or future clinically derived data. This may include important variations necessary for different countries or ethnic groups. It may also include space for new measurements that improve the performance of the method in one or all of the three important criteria mentioned above in the detailed description.

FIGS. 1a and 1b illustrate an overall method in the form of a flowchart, showing how the input and algorithm selection process could be implemented in practice. The method may be carried out through use of a computer suitably programmed to perform the method and each of the above algorithms, as generally shown in FIG. 2. The computer 10 may provide a user with a visual display or other output device 12 and a way for the user to input the various data required by the method, e.g. user input device 14. Exemplary embodiments may include a touchscreen for displaying information and inputting of user data. The computer may be standalone or networked. If networked, the data input by each user may be transmitted to a remote server (not shown) and stored along with data from other users so that statistical analysis on the data can be performed. The computer may be portable, for example in the form of a handheld unit (e.g. a mobile telephone) or notebook computer. The computer may be in the form of a terminal situated at a suitable location such as a supermarket or pharmacy. As will be explained below, the computer may form part of a unit configured to assist a user in selecting items when shopping, particularly for groceries.

An alternative embodiment is where the individual does not need to directly input some or all relevant data, but it is transferred electronically from another device, such as from a blood pressure monitor 20, weighing scales 22, breath analyser 24 or cholesterol test machine 26. The data transfer may be through physical connection, such as through a computer USB port or through a wireless connection, e.g. wireless connection network 30. The computer 10 receiving the data may be portable or part of a terminal situated at a suitable location such as a supermarket or pharmacy. It may also be part of a network where data are transferred from another database storing the values required to calculate heart age and/or heart age-associated information, such as diet and lifestyle data. The major advantage of this embodiment is the automated calculation of heart age values, reducing the time taken by a consumer in data entry.

The computer 10 implementing the method of FIGS. 1a and 1b provides a database or memory 16 in which is stored a plurality of algorithms 18, as discussed above and a processor that implements an algorithm selection process 11, as will be described.

It is to be understood that the flowchart in FIGS. 1a and 1b illustrates merely one particular method of arriving at a choice of one of the above algorithms. Other methods are possible, provided they also arrive at an algorithm appropriate for the data input by a user or transferred from a device.

The method begins at step 101 with the user inputting (or a device transmitting) basic non-invasive measures such as their age, gender, weight, height and waist measurements. The weight and height measurements can be used in the method to calculate the user's body mass index (BMI), which is typically calculated by dividing the square of the user's height (in meters) by their weight (in kilograms), although the method includes a capability to convert imperial measures into metric format. A normal range for BMI is typically between 20 and 25. A higher BMI is associated with an increased risk of CVD, and is consequently included in some of the algorithms for calculating heart age, as described above. The measures inputted are stored for future use.

At step 102, the user is presented with a question asking them if they have been diagnosed with cardiovascular disease. If the user's answer is yes, the method proceeds to step 103, and displays a message to the user indicating that the tool is unsuitable for them. Further messages may optionally be displayed, such as a recommendation to follow clinical advice regarding their condition. The method then ends.

Alternatively, if the user answers no to the question at step 102, the user is then asked to input (step 104) their diabetes status and smoking status, i.e. whether they have and diabetes condition and whether they have smoked in the past year, providing in each case a yes or no answer. If the input is from a breath analyser, a threshold level of carbon monoxide or cotinine can be used to determine the smoking status. These answers are stored for future use. The method proceeds to step 105, where the user is asked for their total cholesterol reading, if they know it. If this is not known, the method proceeds to step 106, where algorithm 3 is provisionally selected. If the user knows their total cholesterol, the method proceeds to step 107, where the user is asked to input their HDL cholesterol reading, if they know it. If this is not known, the method proceeds to step 108, where algorithm 2 is provisionally selected. If the user knows their HDL cholesterol reading, the method proceeds to step 109, where algorithm 1 is provisionally selected. For all these blood-derived measurements (total and HDL cholesterol, diabetes diagnosis), data output from a clinical chemistry analyser (portable or located in a laboratory) can be transferred manually or automatically (e.g. through USB or other cable or wirelessly) to a computer or network.

Regardless of which of algorithms 1, 2 or 3 is provisionally selected, the method then proceeds to step 110, where the user is asked for their systolic blood pressure reading. If this is known, the method proceeds to step 114, where the user is asked for their treatment status, i.e. if they are currently taking antihypertensive medication. Depending on the user's answer, whether the user is on blood pressure treatment 115 or not on blood pressure treatment 116, the appropriate version of the algorithm (being the provisionally selected choice of 1, 2 or 3) is finally selected. The blood pressure may be measured using an electronic blood pressure monitor and transferred manually or automatically (e.g. through USB or cable or wirelessly) to a computer or network.

If, at step 110, the user's systolic blood pressure is not known, the method instead proceeds to step 111, where a choice is made dependent on whether the user inputted a value for their HDL cholesterol at step 107. If an input was made, the method proceeds to step 112, and algorithm 4 is finally selected in place of the provisional selection made earlier. If no value for HDL was entered, the method proceeds to step 113, where a choice is made dependent on whether the user inputted a value for their total cholesterol at step 105. If an input was made, the method proceeds to step 117, and algorithm 5 is finally selected in place of the provisional selection made earlier. If no value for total cholesterol was entered, the method proceeds instead to step 118, and algorithm 6 is finally selected in place of the provisional selection made earlier.

For all algorithm selections, the method then proceeds to step 119, shown in FIG. 1b, where the user is asked to input information relating to their diet. This may include information relating to consumption frequency of foods low in saturated fat, foods low in salt, frequency of calorie restriction, frequency of consuming five portions of fruit and vegetables per day, frequency of fast food choices and other data providing indications of the user's diet. At step 120, the user is requested to input further information regarding exercise and physical activity, for example how often the user takes exercise and at what level. At step 120, the method then calculates a diet score based on the dietary information input at steps 119 and 120 and a physical activity score based on the physical activity information input at steps 119 and 120. Frequency responses on questions are converted into a point score. For example, a user may be asked if they consume foods low in saturated fat on 0 to 1 days, 2 to 4 days or greater than or equal to 5 days a week. A healthier response is indicated by a greater frequency of healthy choice e.g. choosing foods low in saturated fat on 5 days a week rather than 0 to 1 day a week. A score for each question can be computed and saved to a database. In addition a "diet score" can be created that integrates all "healthy" diet responses into a summary measure. This is achieved through simple addition of scores for each question. However, it will be understood that alternative scoring methods can be deployed to create different scores where the responses on each question are weighted according to their relative importance. For example, if an individual is overweight, questions about calories may be given extra weighting in a summary diet score. A physical activity score is computed by giving more points for increased frequency and intensity of reported activity.

An alternative embodiment is where the individual does not directly input relevant dietary data, but it is transferred from another database, such as from a storecard, or an online database of food purchase data. The data transfer may be through physical connection, such as through a computer USB port or through a wireless connection. The computer receiving the data may be portable or part of a terminal situated at a suitable location such as a supermarket or pharmacy. It may also be part of a network where data are transferred from another database storing the values required to calculate heart age and/or heart age-associated information, such as diet and lifestyle data. A major advantage of this embodiment is the automated calculation of heart age values, reducing the time taken by a consumer in data entry.

Steps 119, 120 and 121 are, however, optional and are not needed for the calculation of CVD probability and heart age.

At step 122 the method then proceeds to calculate the user's heart age, based on the input data and the particular algorithm selected based on the user's inputs. The heart age is displayed to the user, along with other information dependent upon various of the user's inputs. At step 123, a decision is made dependent upon the user's input at step 104, i.e. whether the user is a smoker or not. If so, a smoking message is incorporated into the display containing the user's heart age. The message may comprise information regarding ways to quit smoking, and the benefits that might result, which would be indicated by a reduction in their heart age.

At step 125 a decision is made dependent upon the user's input at step 101, in particular the user's height, weight and waistline measurement, to determine whether the user is classified as being overweight. If so, a further message is incorporated into the display containing the user's heart age. This message may comprise information regarding ways to lose weight, and the benefits that might result, which would be indicated by a reduction in their heart age.

At step 127, a general message relating to the user's heart age is incorporated into the display, for example relating to what this means and what the user could do to reduce it. Further messages may be displayed at step 128 before the end of the program 129 relating to various risk factors identified by the method, and relating to changes in diet, physical activity and lifestyle that are recommended, for example based on the user's inputs at steps 119-121 earlier. Such messages, provided by a message store 19, may also be accompanied by recommended next steps, such as ordering food products online that would lead to improvements in the dietary scores. For example, a user who reports infrequent choice or consumption of foods lower in saturated fat may be advised to switch food products ordered in an online retail environment to comply more closely with recommended dietary guidelines (e.g. foods lower in saturated fat). This may be extended to a range of nutrients, including but not restricted to total fat, type of dietary fat, increased fruit and vegetables, oily fish, salt, calorie level or individual food products, such as those containing functional ingredients designed to lower a cardiovascular risk factor. Larger changes may be suggested, such as recommending the user creates a personalised dietary plan or follows a more restrictive calorie-controlled dietary regime or a personalised physical activity regime. Feedback from the online shopping environment would embody a form of data input as described in step 119.

Thus, steps 124 to 128 exemplify the selection of one or more messages for output to the user from a set of possible messages based on the calculated heart age. The messages selected may also be based on the heart age calculation algorithm selected.

Aspects of the method described above can also be used in estimating a user's HDL cholesterol level when the total cholesterol is either known or unknown. In a first method, the estimated CVD risk is determined according to the available information, using one of the above described algorithms, for example when the factors TOT, SBP, diabetes status, smoking status, age, gender and BMI are known. The calculated CVD risk estimate is then inserted into the relevant one of equations 1 to 4 above, and the equation solved to obtain a value for HDL cholesterol. The value for HDL may be found through use of an iterative solving method.

In a second method, total cholesterol level is not known. The estimated CVD risk is calculated according to the information available, for example SBP, diabetes status, smoking status, age, gender and BMI. The CVD risk estimate is inserted into the relevant one of equations 1 to 4 and the equation solved for HDL, i.e. producing a number for HDL that would produce that same risk level. A default value for the total cholesterol (TOT) may be used based on the user's age and gender. Given that the ratio of total to HDL cholesterol is generally of more importance than the absolute individual totals, using an estimate based on age and gender does not in this case greatly impact on the accuracy of the result.

In a third method, total cholesterol level is not known. The estimated CVD risk is calculated according to the information available, for example SBP, diabetes status, smoking status, age, gender and BMI. The CVD risk estimate is inserted into the relevant one of equations 1 to 4 and a range of possible values for total cholesterol level and HDL level calculated that would solve the equation for CVD risk, i.e. producing ranges of values of total cholesterol and HDL that would produce that same risk level. A default value for the total cholesterol (TOT) may be used based on the user's age and gender and the equation then solved for HDL.

Using the above methods, an indication may be provided to the user regarding whether a cholesterol test is advised, for example if the estimated CVD risk reaches a threshold level where medical guidelines suggest a test is advisable.

Certain aspects of the method described above are particularly suited for being implemented in an apparatus for assisting a user in making beneficial food choices while shopping. Such an apparatus may be in the form of a handheld computing device, which may advantageously comprise a card reader or a barcode reader, the card reader allowing a user to input his or her personal information into the apparatus, and a barcode reader allowing the user to scan items while shopping to determine whether they fit with recommendations dependent upon the user's profile. The apparatus, having been suitably programmed with information relating to the user, can be configured to recommend a maximum proportion of saturated fat in the user's diet based on the user's heart age, and as a result can flag certain items to the user while they are shopping. For example, if the user scans a pack of full fat butter, the apparatus could indicate that an alternative brand would be more suitable for them, such as a low fat spread or a cholesterol-lowering spread.

The apparatus allows food products chosen by the user to be compared to a required nutritional standard determined by the user's heart age. For example, saturated fat being <7% of calories if the user's heart age is very high, <10% of calories if the heart age is modestly high, or <15% of calories if the heart age is normal or low. Dietary attitudes may also be incorporated into recommendations made to the user. For example, if the user is not interested in much change, the apparatus may choose similar food products within a given food category. If the user desires dietary change, food products may be chosen to feature other alternative and healthier food categories.

A mobile phone or other device could contain a bar code with heart age information. Scanning the bar code at a supermarket checkout, or on entry to a supermarket could provide recommendations or product promotions in keeping with the individual's heart age requirements. Alternatively the information could be held on a store card and entered into a kiosk that personalised product promotions based on the heart age and lifestyle input.

The apparatus may also be configured to produce a list of recommended food items, from which the user can select while shopping. Certain of the recommended items may be associated with vouchers to provide selective discounts to the user.

In practice, the user's information may be input separately from the point of use of the apparatus. For example, the information may be input online as described in step 119 and then downloaded to the apparatus either directly through the user's personal card or by the card being uniquely identified with the user and the apparatus downloading the required information when the user is identified. The user may alternatively be identified to the apparatus through other means such as biometric information or other items uniquely identified with the user such as a key, a mobile telephone or a token.

An alternative embodiment may involve the user carrying out the steps of inputting their information as well as shopping online, either through a single web site or through associated web sites, a first web site dealing with the user's information and providing a heart age and associated guidance, and a second web site providing an online shopping service. Information provided by the heart age method may be used while the user is shopping online, in a similar way to the apparatus described above. The user may be presented with automated information or vouchers depending on the items they choose and their heart age profile. In this way, the user can be guided towards selecting a range of purchases more suited to their particular profile.

Other embodiments are intentionally within the scope of the invention, as defined by the appended claims.

The invention claimed is:

1. An automated method of determining a measure of a subjects heart age, said method carried out by a computer system and comprising the steps of:
receiving a plurality of inputs, each relating to an attribute of the subject, each attribute defining one or more of a demographic status of the subject, a lifestyle status of the subject, a physical condition of the subject and a medical history of the subject, said inputs either provided through a user input device of the computer system or transferred electronically from another device, wherein said inputs do not include any quantitative measure of a cholesterol level of the subject;

determining from said received inputs, a set of parameters for which input data has been received as input;

selecting according to said set of parameters, a heart age calculation algorithm from a predetermined set of heart age calculation algorithms stored in a database on the computer system, wherein the selecting is implemented by a processor of the computer system, wherein the predetermined set of heart age calculations include at least one non-cholesterol-based algorithm that does not contain a cholesterol level as a parameter;

calculating a heart age for the subject according to the selected algorithm; and providing as output said calculated heart age on a visual display of the computer system.

2. The method of claim 1 further including the step of selecting one or more messages for output to the user based on the calculated heart age from a set of possible messages stored on the computer system in a message store.

3. The method of claim 2 in which the step of selecting one or more messages is further based on the heart age calculation algorithm selected.

4. The method of claim 1 in which the non-cholesterol-based algorithm further uses height and weight as parameters.

5. The method of claim 1 in which the non-cholesterol-based algorithm further uses waist size as a parameter.

6. The method of claim 1 further including the step of notifying a user of one or more factors contributory to a high heart age.

7. The method of claim 1 further including a step of presenting the user with a number of options for reducing heart age.

8. The method of claim 1 further including a step of recording a plurality of said calculated heart ages for the subject over a period of time.

9. The method of claim 1 further including the steps of:
calculating a subjects heart age for a plurality of subjects;
storing the calculated heart ages for a plurality of subjects; and
calculating average heart ages as a function of one or more of said attributes of the plurality of subjects.

10. The method of claim 9 in which said one or more of said attributes comprise demographic attributes.

11. The method of claim 9 in which said one or more of said attributes comprise lifestyle attributes.

12. The method of claim 9 in which the plurality of inputs relating to attributes of the subject are selected from: height, weight, gender, blood pressure, age, incidence of smoking activity, incidence of a diabetic condition, incidence of hypertensive condition or antihypertensive treatment, waist size, incidence of CVD, total cholesterol level, HDL cholesterol level, incidence of blood pressure condition or treatment, calorie intake, saturated fat intake, salt intake, level of physical activity.

13. The method of claim 1 further including the step of determining one of a plurality of different sets of constants to use in the selected algorithm based on the gender of the subject.

14. The method of claim 1 further including the step of determining one of a plurality of different sets of constants to use in the algorithms based on the incidence of antihypertensive treatment for the subject.

15. The method of claim 1 in which the heart age calculation algorithms each comprise a first stage to calculate a probability value for coronary heart disease followed by a second stage to calculate heart age therefrom.

16. The method of claim 1 wherein the at least one non-cholesterol algorithm is at least one of the following algorithms:
Algorithm 3 which determines the subject's heart age from the following set of parameters: age, gender, incidence of diabetes, incidence of smoking, incidence of hypertensive condition, systolic blood pressure and body mass,
Algorithm 6 which determines the subject's heart age from the following set of parameters: age, gender, incidence of diabetes, incidence of smoking, incidence of hypertensive condition, and body mass.

17. A non-transitory computer-readable medium comprising a computer program of claim 1.

18. Apparatus for determining a measure of a subject's heart age, the apparatus comprising:
means for receiving a plurality of inputs, each relating to an attribute of the subject, each attribute defining one or more of a demographic status of the subject, a lifestyle status of the subject, a physical condition of the subject and a medical history of the subject, said inputs not including a quantitative measure of cholesterol;
means for determining from said received inputs, a set of parameters for which input data has been received;
means for selecting a heart age calculation algorithm from a predetermined set of heart age calculation algorithms according to said set of parameters, wherein the predetermined set of heart age calculations include at least one non-cholesterol-based algorithm that does not contain a cholesterol level as a parameter;
means for calculating a heart age for the subject according to the selected algorithm; and
means for providing as output said calculated heart age.

19. The apparatus of claim 18 wherein the at least one non-cholesterol algorithm is at least one of the following algorithms:
Algorithm 3 which determines the subject's heart age from the following set of parameters: age, gender, incidence of diabetes, incidence of smoking, incidence of hypertensive condition, systolic blood pressure and body mass,
Algorithm 6 which determines the subjects heart age from the following set of parameters: age, gender, incidence of diabetes, incidence of smoking, incidence of hypertensive condition, and body mass.

* * * * *